(12) United States Patent
Chen et al.

(10) Patent No.: US 12,036,122 B2
(45) Date of Patent: Jul. 16, 2024

(54) REPAIR DEVICE FOR TREATMENT OF TRICUSPID REGURGITATION

(71) Applicant: Shanghai ConFlow MedTech Co., Ltd., Shanghai (CN)

(72) Inventors: Xiumin Chen, Shanghai (CN); Qing Li, Shanghai (CN); Baicheng Hu, Shanghai (CN)

(73) Assignee: SHANGHAI CONFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 17/909,395

(22) PCT Filed: Aug. 23, 2021

(86) PCT No.: PCT/CN2021/113973
§ 371 (c)(1),
(2) Date: Sep. 5, 2022

(87) PCT Pub. No.: WO2023/015601
PCT Pub. Date: Feb. 16, 2023

(65) Prior Publication Data
US 2024/0197474 A1 Jun. 20, 2024

(30) Foreign Application Priority Data
Aug. 11, 2021 (CN) .......................... 202110918432.0

(51) Int. Cl.
*A61F 2/24* (2006.01)
*A61L 27/14* (2006.01)
*A61L 27/36* (2006.01)

(52) U.S. Cl.
CPC ............ *A61F 2/246* (2013.01); *A61F 2/2466* (2013.01); *A61L 27/14* (2013.01); *A61L 27/3625* (2013.01);
(Continued)

(58) Field of Classification Search
CPC .................. A61F 2/246; A61F 2/2466; A61F 2210/0014; A61F 2220/0016; A61F 2220/0075; A61L 27/14; A61L 27/3625
See application file for complete search history.

(56) References Cited

U.S. PATENT DOCUMENTS

2008/0208328 A1    8/2008   Antocci et al.
2016/0030169 A1    2/2016   Shahriari
(Continued)

FOREIGN PATENT DOCUMENTS

CN      110418623 A     11/2019
CN      211325271 U     8/2020
(Continued)

*Primary Examiner* — Suzette J Gherbi
(74) *Attorney, Agent, or Firm* — Bayramoglu Law Offices LLC

(57) ABSTRACT

A repair device for treatment of tricuspid regurgitation includes a support frame, an occlusive membrane, and a suture line. The support frame includes a central shaft and anchoring members that are disposed around the central shaft and radially unfolded for anchoring leaflets of a tricuspid valve. The occlusive membrane surrounds connections between the anchoring members and the central shaft, and the occlusive membrane is connected to the support frame through the suture line. A semi-closed space surrounding the central shaft is formed by an outer side wall of the central shaft, the anchoring members and the occlusive membrane, and has a closed end in proximity to a ventricle and an open end in proximity to an atrium. The central shaft has a closed end in proximity to the ventricle. The repair device for treatment of tricuspid regurgitation reduces the number of implants, thereby reducing the side effects caused by implantation.

10 Claims, 6 Drawing Sheets

(52) U.S. Cl.
CPC .............. *A61F 2210/0014* (2013.01); *A61F 2220/0016* (2013.01); *A61F 2220/0075* (2013.01)

(56) References Cited

U.S. PATENT DOCUMENTS

| | | |
|---|---|---|
| 2018/0161035 A1 | 6/2018 | Greenberg et al. |
| 2018/0296334 A1* | 10/2018 | Dixon ................ A61B 17/1285 |
| 2019/0000613 A1* | 1/2019 | Delgado ............ A61B 17/3468 |
| 2019/0008635 A1 | 1/2019 | Francis et al. |
| 2019/0209323 A1* | 7/2019 | Metchik .................. A61F 2/246 |
| 2019/0321166 A1 | 10/2019 | Freschauf et al. |
| 2022/0287841 A1* | 9/2022 | Freschauf ............. A61F 2/2466 |
| 2023/0190468 A1* | 6/2023 | Chen ....................... A61F 2/246 |
| | | 623/2.1 |
| 2024/0065836 A1* | 2/2024 | Popp ................. A61M 25/0023 |
| 2024/0108322 A1* | 4/2024 | Chen .................... A61F 2/2466 |

FOREIGN PATENT DOCUMENTS

| | | |
|---|---|---|
| CN | 111616835 A | 9/2020 |
| WO | 2010098804 A1 | 9/2010 |

\* cited by examiner

REPAIR DEVICE FOR TREATMENT OF TRICUSPID REGURGITATION

CROSS REFERENCE TO THE RELATED APPLICATIONS

This application is the national phase entry of International Application No. PCT/CN2021/113973, filed on Aug. 23, 2021, which is based upon and claims priority to Chinese Patent Application No. 202110918432.0, filed on Aug. 11, 2021, the entire contents of which are incorporated herein by reference.

TECHNICAL FIELD

The present disclosure relates to a repair device for treatment of tricuspid regurgitation and belongs to the technical field of medical devices.

BACKGROUND

Tricuspid regurgitation (TR) is a common heart valve disease. In severe cases, TR can lead to decreased cardiac output and systemic congestion, and it signifies poor prognosis in many cardiac diseases and is closely related to the prognosis of patients. Surgery is currently the mainstream method to treat TR, but it has the disadvantages of using large incisions, has many complications, has high mortality, etc. Therefore, considering the limitations of surgery, it is necessary to develop a TR treatment method that uses small incisions, is simple, and has fewer complications in this technical field.

In the past 10 years, with the development of biomedical materials and medical imaging, breakthroughs have been made in transcatheter valve replacement and repair, making it a hot spot in interventional cardiology. At present, the most developed interventional repair technology for tricuspid valve is edge-to-edge repair, which is found in Abbott's MitraClip (PCT/USA2009/068023) and Edwards PASCAL (US2019/0321166A1). However, TR mostly originates from the central region of the three leaflets, while the edge-to-edge repair technique can only clamp the peripheral region of the leaflets, which has a limited effect, and many clips are often required to be implanted. There are also some designs targeting the central regurgitation zone of the tricuspid valve, but these designs are flawed, and thus have not really been used clinically. In addition, there are some patents relating to mitral and tricuspid valve repair devices, but the prior designs and products require complex structures and components to achieve edge-to-edge repair of valves. The complex design increases the difficulty of the device fabrication process and puts forward higher requirements for the surgeon, thereby introducing more risk points. Therefore, there is an urgent need for a repair device for treatment of tricuspid regurgitation, which is simple to fabricate and operate, safe and reliable, and has an excellent therapeutic effect.

SUMMARY

In order to overcome the deficiencies of the prior art, an objective of the present disclosure is to provide a repair device for treatment of tricuspid regurgitation that has a simple fabrication process, few implants, firm fixation, and desired effect of reducing tricuspid regurgitation (TR).

In order to achieve the above objective, the present disclosure adopts the following technical solution. A repair device for treatment of tricuspid regurgitation is delivered to leaflets of a tricuspid valve through a delivery system and includes a support frame, an occlusive membrane, and a suture line, where the support frame includes a central shaft and anchoring members that are disposed around the central shaft and radially unfolded for anchoring the leaflets of the tricuspid valve. The occlusive membrane surrounds the connections between the anchoring members and the central shaft that are on an outer side wall of the central shaft, and the occlusive membrane is connected to the support frame through the suture line. A semi-closed space surrounding the central shaft is formed by the outer side wall of the central shaft, the anchoring members, and the occlusive membrane and has a closed end in proximity to a ventricle and an open end in proximity to an atrium. The central shaft has a closed end in proximity to the ventricle.

Preferably, the anchoring members each have one end fixedly connected to the central shaft and the other end radially unfolded away from the central shaft. The end of the anchoring member fixedly connected to the central shaft may be provided with a hole for threading the suture line.

Preferably, the anchoring members may include a plurality of clamp arm sets; the clamp arm set may include two clamp arms, namely, an upper clamp arm and a lower clamp arm, which may be configured to cooperate with each other to open and close. The clamp arm may be provided with barbs. The occlusive membrane may be provided between any adjacent clamp arm sets around the central shaft. An edge of the clamp arm may be provided with a hole for threading the suture line. The clamp arm may be further provided with a pull hole for threading a pull string configured to fold and unfold the clamp arm.

Preferably, the clamp arm may include a fixed connection section with an end in proximity to the ventricle and fixedly connected to the central shaft and a separation section formed by extending from the fixed connection section to the atrium. An edge of each of the fixed connection section, the separation section, and a transition section between the fixed connection section and the separation section may be provided with a hole for threading the suture line.

Preferably, the hole for threading the suture line may include a plurality of round holes or a slot hole.

Preferably, the support frame may be integrally formed by cutting a metal tube, or by heat-setting a memory metal after laser cutting or wire cutting, and has a function of shape memory.

Preferably, the occlusive membrane may be made of a flexible occlusive material and may include an animal pericardial membrane, an animal valve membrane, a polyethylene terephthalate (PET) membrane, a polytetrafluoroethylene (PTFE) membrane, a polyurethane (PU) membrane, or a polyester fiber braided membrane.

Preferably, the suture line may be made of nylon or a nitinol wire.

Preferably, the occlusive membrane may be an integrally formed membrane and may include a closed bottom cover for covering the end of the central shaft in proximity to the ventricle, a waist wrapping the outer side wall of the end of the central shaft in proximity to the ventricle, and branches between adjacent clamp arm sets. Alternatively, a transition portion may be further provided between the waist and the branches.

Preferably, the occlusive membrane may include a plurality of membrane sheets, and the plurality of membrane sheets may be sutured to the support frame through the suture line.

Compared with the prior art, the present disclosure has the following beneficial effects:

The repair device for treatment of tricuspid regurgitation of the present disclosure includes only the occlusive membrane and the support frame, which reduces the number of implants, thereby reducing the side effects caused by implantation. Through the anchoring members, the occlusive membrane is stabilized in the center of the leaflets of the tricuspid valve to effectively reduce regurgitation in the center of the leaflets of the tricuspid valve. In addition, the occlusive membrane can be flexibly tightly sutured to the support frame to improve the occlusion effect. In addition, the repair device for treatment of tricuspid regurgitation of the present disclosure has excellent elastic properties, is convenient for contraction and retrieval, and simplifies the actual surgical operation process.

Figure 1:
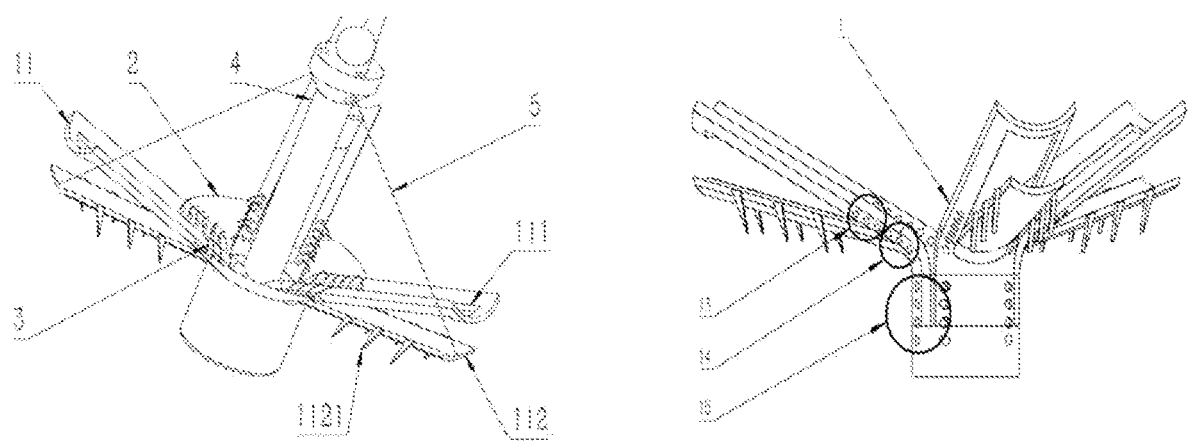
FIG. 1 is a schematic view of a repair device for treatment of tricuspid regurgitation according to the present disclosure.

Reference Numerals: 1. support frame; 11. anchoring member; 111. lower clamp arm; 112. upper clamp arm; 1121. barb; 13. upper hole; 14. middle hole; 15. lower hole; 16. slot hole; 2. occlusive membrane; 21. bottom cover; 22. waist; 23. branch; 24. tapered section; 25. membrane sheet; 3. suture line; 4. central shaft; 5. pull string; 6. heart; 61. leaflet of tricuspid valve; and 7. repair device for treatment of tricuspid regurgitation.

DETAILED DESCRIPTION OF THE EMBODIMENTS

In order to make the present disclosure more understandable, the preferred embodiments of the present disclosure are described in detail below with reference to the drawings.

As shown in FIGS. 1 to 12, the present disclosure provides a repair device for treatment of tricuspid regurgitation, which is delivered to leaflets 61 of a tricuspid valve through a delivery system and includes a support frame 1, an occlusive membrane 2, and a suture line 3. The support frame 1 includes a central shaft 4 and anchoring members 11 that are disposed around the central shaft 4 and radially unfolded for anchoring the leaflets 61 of the tricuspid valve. The occlusive membrane 2 surrounds the connections between the anchoring members 11 and the central shaft 4 that are on an outer side wall of the central shaft 4, and the occlusive membrane 2 is connected to the support frame 1 through the suture line 3. A semi-closed space surrounding the central shaft 4 is formed by the outer side wall of the central shaft 4, the anchoring members 11 and the occlusive membrane 2 and has a closed end in proximity to a ventricle and an open end in proximity to an atrium. The central shaft 4 has a closed end in proximity to the ventricle. The anchoring members 11 each have one end fixedly connected to the central shaft 4 and the other end radially unfolded away from the central shaft 4. The end of the anchoring member 11 fixedly connected to the central shaft 4 is provided with a hole for threading the suture line. The anchoring members 11 include a plurality of clamp arm sets. The clamp arm set includes two clamp arms, namely an upper clamp arm 112 and a lower clamp arm 111, which are configured to cooperate with each other to open and close. The upper clamp arm is provided with barbs 1121. The occlusive membrane 2 is provided between any adjacent clamp arm sets around the central shaft 4. An edge of the clamp arm is provided with a hole for threading the suture line 3. The clamp arm is further provided with a pull hole for threading a pull string 5 configured to fold and unfold the clamp arm. The clamp arm includes a fixed connection section with an end in proximity to the ventricle and fixedly connected to the central shaft 4 and a separation section formed by extending from the fixed connection section to the atrium. An edge of each of the fixed connection section, the separation section, and a transition section between the fixed connection section and the separation section is provided with a hole for threading the suture line 3. The hole for threading the suture line 3 includes a plurality of round holes or a slot hole 16. The support frame 1 is integrally formed by cutting a metal tube, or by heat-setting a memory metal after laser cutting or wire cutting, and has a function of shape memory. The occlusive membrane 2 is made of a flexible occlusive material and includes an animal pericardial membrane, an animal valve membrane, a polyethylene terephthalate (PET) membrane, a polytetrafluoroethylene (PTFE) membrane, a polyurethane (PU) membrane, or a polyester fiber braided membrane, etc. The suture line 3 is made of nylon or a nitinol wire, etc. The occlusive membrane 2 is an integrally formed membrane. It includes a closed bottom cover 21 for covering the end of the central shaft 4 in proximity to the ventricle, a waist 22 wrapping the outer side wall of the end of the central shaft 4 in proximity to the ventricle, and branches 23 between adjacent clamp arm sets. Alternatively, a transition portion is further provided between the waist 22 and the branches 23. The occlusive membrane 2 includes a plurality of membrane sheets, and the plurality of membrane sheets are sutured to the support frame 1 through the suture line 3.

Figure 5:
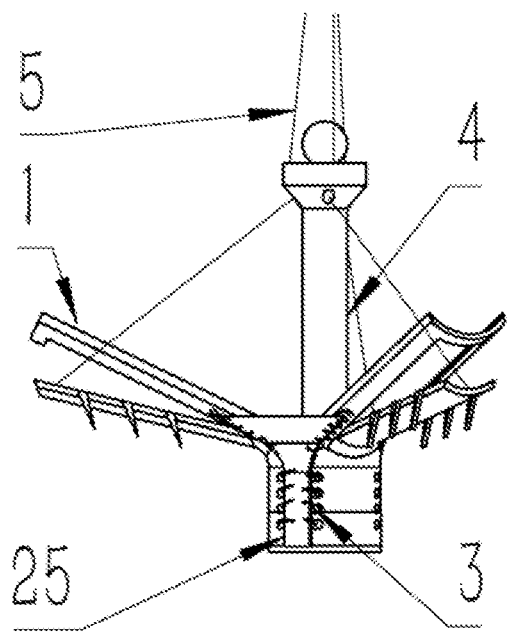
FIG. 5 is a second schematic view showing a suture connection of the occlusive membrane according to the present disclosure.
Figure 6:
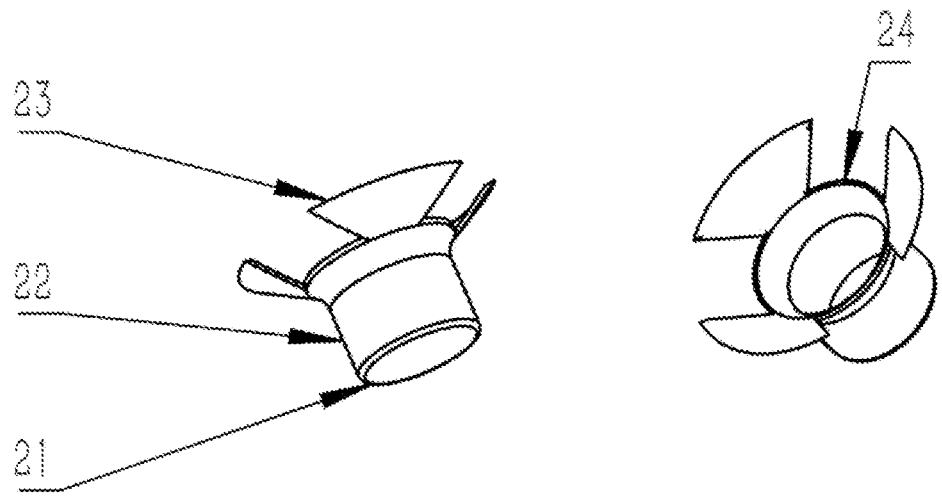
FIG. 6 is a third structural view of the occlusive membrane according to the present disclosure.
Figure 7:
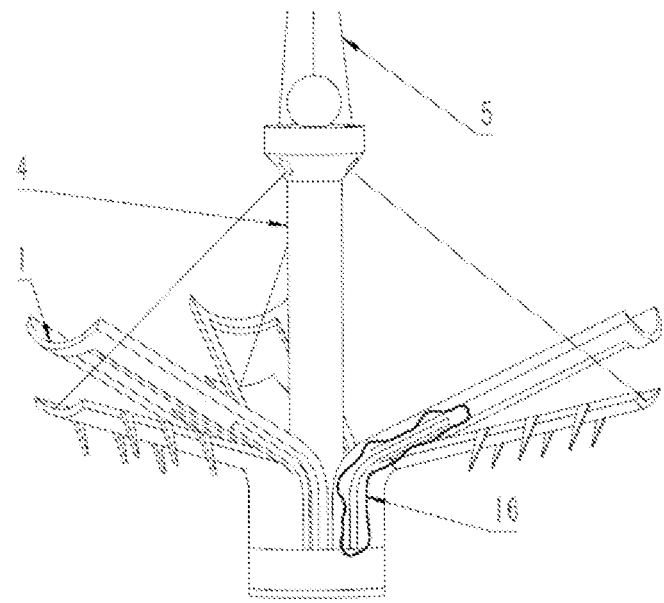
FIG. 7 is a structural view of a support frame with a slot hole according to the present disclosure.

As shown in FIGS. 1 to 12, the present disclosure provides a repair device for treatment of tricuspid regurgitation 7, which includes a support frame 1, an occlusive membrane 2, and a suture line 3 connecting the support frame and the occlusive membrane. The support frame 1 is integrally cut and shaped by a metal tube. The occlusive membrane 2 is made of a flexible occlusive material and may be an animal pericardial membrane, an animal valve membrane, a PET membrane, a PTFE membrane, a PU membrane, a polyester fiber membrane, or other braided membrane. The gaps at the center and the roots of the branches of the support frame 1 are completely covered by the occlusive membrane 2. After the branches of the support frame 1 are grasped and fixed to the tricuspid valve, the occlusive membrane 2 is located at a central position surrounded by the leaflets of the tricuspid valve to fill the space to achieve the purpose of occlusion. The occlusive membrane 2 is fixed through round holes (including an upper hole 13, a lower hole 15, and a middle hole 14, as shown in FIG. 1) or a slot hole (a slot hole 16, as shown in FIG. 7) at a bent edge of the anchoring member 11 on the support frame 1. The occlusive membrane 2 can completely cover the center of the support frame 1 and the root of the anchoring member 11 to repair the defective tricuspid valve. The occlusive membrane 2 is fixed to the support frame 1 by suturing. The suture line 3 may be made of nylon, a braided thread, or a nitinol wire. The occlusive membrane 2 can be formed by cutting and suturing a whole membrane sheet or a plurality of membrane sheets. The occlusive membrane 2 is sleeved onto a lower part of the support frame 1 and is sutured to the hole on the support frame 1 through the suture line 3 to achieve the purpose of occlusion. The support frame 1 includes 2 to 3 anchoring members 11. The upper and lower clamp arms of the anchoring member 11 are cut from the same metal tube. The anchoring members 11 are radially unfolded, and an unfolding angle between the anchoring members 11 can be adjusted to 90°, 120°, 180° and others according to time use situation. The upper clamp arm 112 and the lower clamp arm 111 of the anchoring member 11 are shaped to intersect each other by heat setting to secure the valve. The upper clamp arm 112 and the lower clamp arm 111 are provided with wire pull holes. A pull string 5 is threaded through the pull hole to fold and unfold the clamp arm, thereby grasping and fixing the tricuspid valve.

Embodiment

In order to overcome the deficiencies of the prior art, the present disclosure provides a repair device for treatment of tricuspid regurgitation, which can effectively reduce TR. Herein, "upper end" refers to an end of the implant, namely the repair device for treatment of tricuspid regurgitation facing an atrium, and "lower end" refers to an end of the repair device for treatment of tricuspid regurgitation facing a ventricle.

The repair device for treatment of tricuspid regurgitation 7 includes a support frame 1, an occlusive membrane 2, a central shaft 4, a suture line 3, and a pull string 5. The support frame 1 is integrally cut and shaped by a metal tube. The occlusive membrane 2 is made of a flexible occlusive material and may be an animal pericardial membrane, an animal valve membrane, a PET membrane, a PTFE membrane, a PU membrane, a polyester fiber membrane, or other braided membrane. The pull string 5 has one end fixed to the clamp arm of an anchoring member 11 and the other end threaded through the hole in the central shaft 4 and controlled by a member through a delivery system. The clamp arm grasps and anchors the tricuspid valve by retracting and releasing the pull string 5. The gaps at the center and the roots of the branches of the support frame 1 are completely covered by the occlusive membrane 2. After the branches of the support frame 1 are grasped and fixed to the tricuspid valve, the occlusive membrane 2 is located at a central position surrounded by the leaflets of the tricuspid valve to fill the space to achieve the purpose of occlusion.

As shown in FIG. 1, the repair device includes the support frame 1 and the occlusive membrane 2. The support frame 1 includes anchoring members 11, an upper hole 13, a middle hole 14, and a lower hole 15. The support frame 1 is integrally cut from a nitinol tube. The anchoring member 11 is composed of an upper clamp arm 112 and a lower clamp arm 111. The support frame is provided with three anchoring members 11, and the anchoring members 11 are evenly distributed. The central shaft 4 is located inside the support frame 1 and is provided with a hole for threading the pull string 5. One end of the pull string 5 is fixed to the clamp arm of the anchoring member 11. In actual operation, the upper and lower clamp arms are pulled by the pull string 5 to grasp the leaflets. In a natural state, the upper and lower clamp arms are fixed to the tricuspid valve to achieve the purpose of repair. The occlusive membrane 2 may be an animal pericardial membrane, an animal valve membrane, a PET membrane, a PTFE membrane, a PU membrane, a polyester fiber membrane, or other braided membrane. The occlusive membrane is fixed to the support frame 1 through the upper hole 13, the middle hole 14, and the lower hole 15. Within the coverage of the occlusive membrane 2, the regurgitation in the gap among the leaflets 61 of the tricuspid valve can be prevented.

Figure 2:
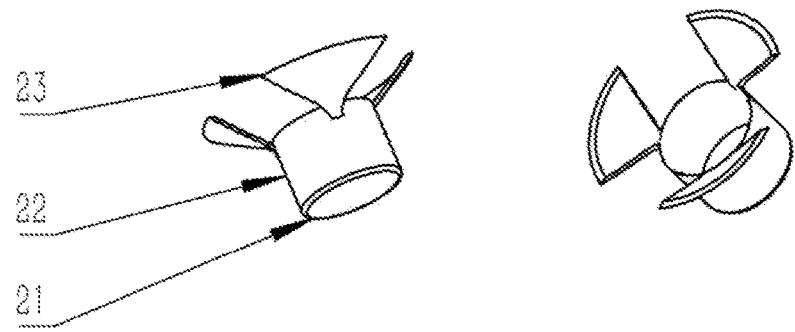
FIG. 2 is a first structural view of an occlusive membrane according to the present disclosure.

FIG. 2 shows a structure of an occlusive membrane. In this structure, the occlusive membrane 2 is composed of a bottom cover 21, a waist 22, and branches 23. There are three branches 23, the size of which is determined according to the gap of the anchoring members 11 of the support frame 1. Optionally, the bottom cover 21, the waist 22 and the branches 23 may be cut out of the same material. In this way, the assembly of the occlusive membrane is simplified, and the overall occlusion performance is improved. In other embodiments, the bottom cover 21 and the waist 22 may be made of a material with higher strength and better fit performance (such as a metal woven mesh or PTFE). The branches 23 can be made of a biological material with better occlusion performance or a polymer material such as PET. Then the two different materials are assembled into a desired shape by stitching.

Figure 3:
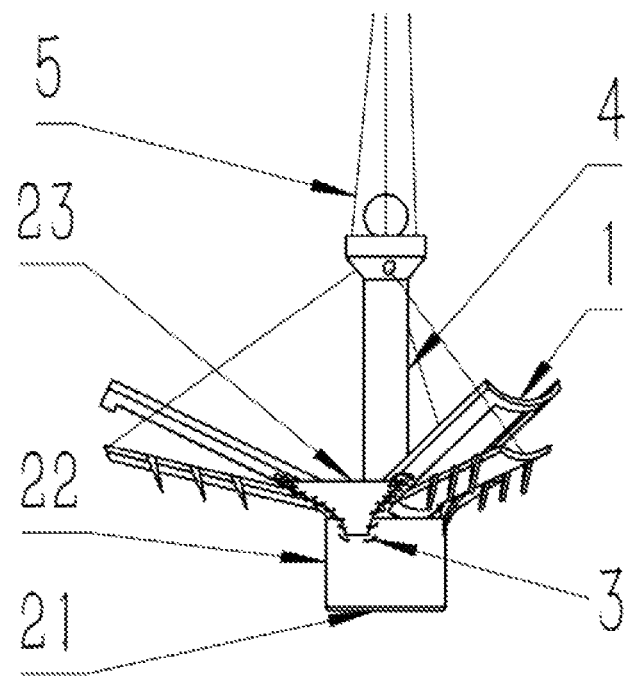
FIG. 3 is a first schematic view showing a suture connection of the occlusive membrane according to the present disclosure.

FIG. 3 shows a suture connection between the occlusive membrane 2 and the support frame 1 shown in FIG. 2. The occlusive membrane 2 is sleeved onto the lower end of the support frame 1 to completely cover the central part of the support frame 1. The edge of the occlusive membrane 2 is sutured to the support frame 1 by the suture line 3. The suture line 3 is threaded through the upper hole 13, the middle hole 14, and the lower hole 15 of the support frame 1 to suture the edge of the occlusive membrane 2. The size of the occlusive membrane 2 is adjustable according to the support frame 1 to make it completely fit with the support frame to improve the occlusion effect.

Figure 4:
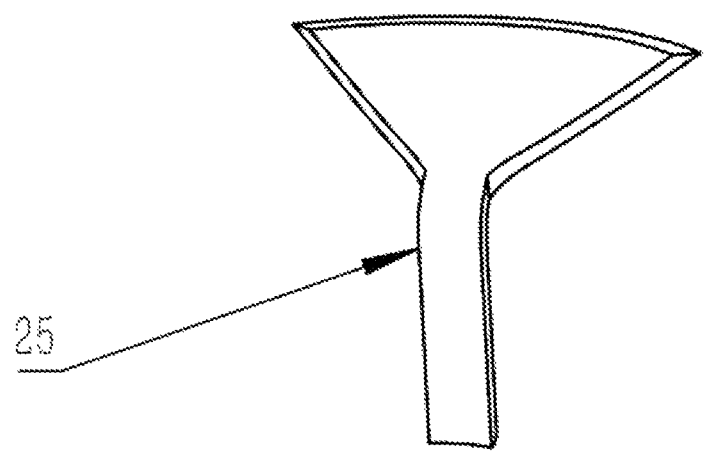
FIG. 4 is a second structural view of the occlusive membrane according to the present disclosure.

FIG. 4 shows another optional occlusive membrane structure. A branch 25 has an upper end in the shape of an inverted triangle and a lower end provided with a rectangular protruding section. In actual assembly, the three branches 25 are assembled together. The occlusive membrane structure reduces the splicing between different membrane sheets and can be sutured to the support frame 1. This design reduces damage to the occlusive membrane and simplifies the fabrication process.

FIG. 5 shows the suture connection between the branch 25 shown in FIG. 4 and the support frame 1. In this design, the central part of the support frame 1 may be blocked mechanically or by other means. The branches 25 mainly cover the gaps between adjacent anchoring members 11. The edge of the occlusive membrane 2 is sutured to the support frame 1 by the suture line 3. Specifically, the suture line 3 is threaded through the upper hole 13, the middle hole 14, and the lower hole 15 of the support frame 1 and is sutured to the edges of the two sides of the inverted triangle of the occlusive membrane.

FIG. 6 shows another optional occlusive membrane structure. In this structure, a tapered section 24 is added on the basis of the occlusive membrane structure shown in FIG. 2. This tapered section matches the arc of the root of the anchoring member 11 of the support frame 1. When the occlusive membrane 2 and the support frame 1 are sutured, the tapered section 24 can fit with the support frame to improve the occlusion effect.

FIG. 7 shows the support frame 1 with the slot hole 16. During assembly, the slot hole 16 for assembling the occlusive membrane 2 reduces the restriction on the number of stitches of the suture line 3. Tighter stitches can be used to assemble the occlusive membrane 2 and the support frame 1 together.

Figure 8:
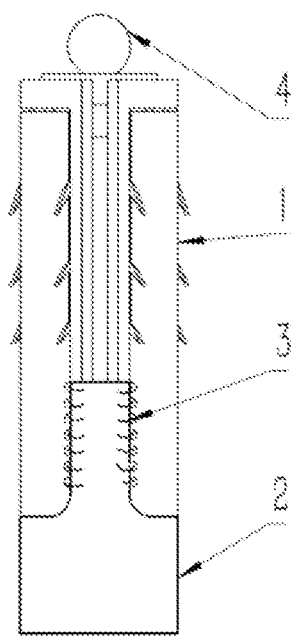
FIG. 8 is a schematic view showing a first configuration of the repair device for treatment of tricuspid regurgitation according to the present disclosure.

FIG. 8 shows a first configuration of the repair device for treatment of tricuspid regurgitation 7 of the present disclosure during delivery, and FIG. 1 shows a second configuration of the repair device for treatment of tricuspid regurgitation that is naturally unfolded after being released from the delivery system. In the first configuration, the repair device for treatment of tricuspid regurgitation 7 is compressed into a strip and inserted into a delivery sheath. The flexible occlusive membrane 2 is foldable, and the upper clamp arm 112 and the lower clamp arm 111 are folded toward the central shaft 4 to be received into the delivery system. In the second configuration, the repair device for treatment of tricuspid regurgitation 7 is released from the delivery system and unfolded naturally. In this configuration, the three pairs of upper and lower clamp arms are radially unfolded at the outer periphery of the central shaft 4, and the occlusive membrane 2 fills the gaps between adjacent pairs of upper and lower clamp arms.

Figure 9:
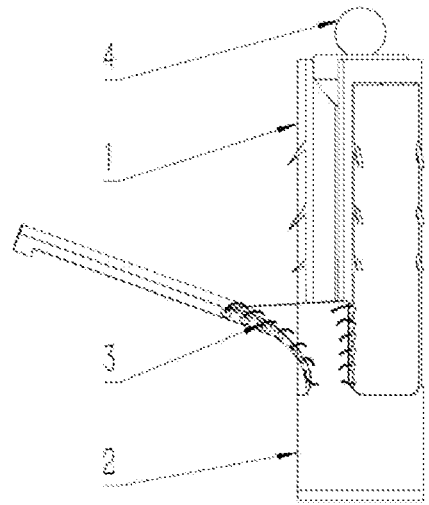
FIG. 9 is a schematic view showing that a lower clamp arm of the repair device for treatment of tricuspid regurgitation is unfolded according to the present disclosure.
Figure 10:
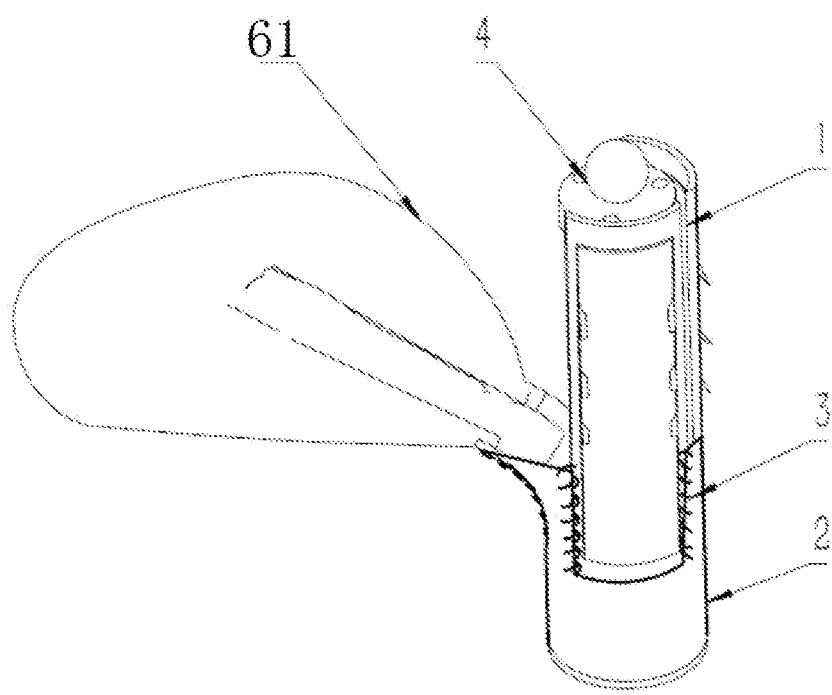
FIG. 10 is a schematic view showing that the lower clamp arm of the repair device for treatment of tricuspid regurgitation grasps and anchors a leaflet of a tricuspid valve according to the present disclosure.
Figure 11:
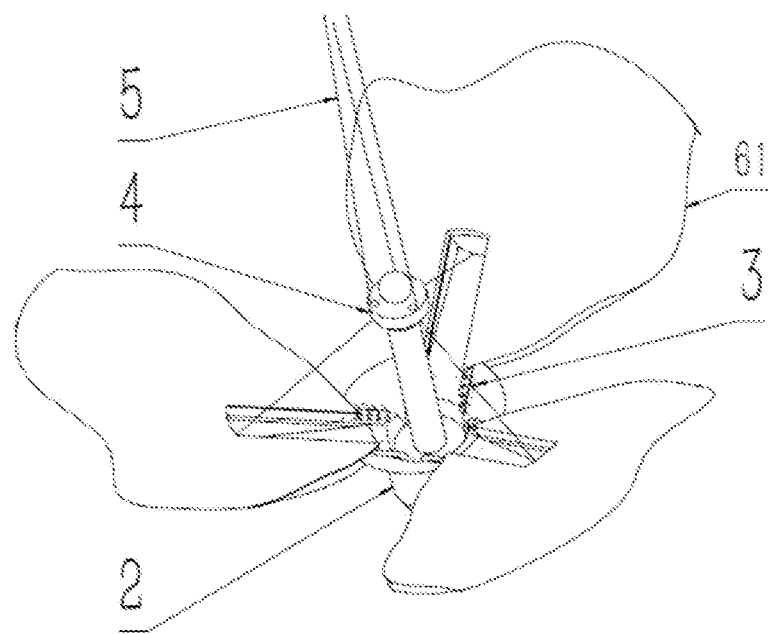
FIG. 11 is a schematic view showing that the repair device for treatment of tricuspid regurgitation is anchored to the leaflets of the tricuspid valve according to the present disclosure.

FIG. 9 shows step-by-step clamping and fixation of the repair device for treatment of tricuspid regurgitation 7 during implantation. First, the repair device for treatment of tricuspid regurgitation is delivered to an intended location (a right ventricle) by the delivery system. One of the lower clamp arms 111 is released by a drive member of the delivery system. Then, the position of the repair device for treatment of tricuspid regurgitation in a heart 6 is adjusted by a control member of the delivery system, such that a target leaflet of the tricuspid valve is placed on the lower clamp arm 111. The upper clamp arm 112 is released to a natural state, and the barbs 1121 on the unfolded upper clamp arm 112 hook the leaflet of the tricuspid valve to prevent it from slipping out between the upper and lower clamp arms (FIG. 10). Since the upper and lower clamp arms are integrally connected and shaped, the upper and lower clamp arms in the natural state clamp the corresponding leaflet of the tricuspid valve. In this way, the repair device for treatment of tricuspid regurgitation can be effectively anchored in the center of the leaflets of the tricuspid valve even when the heart is beating, as shown in FIG. 11.

Figure 12:
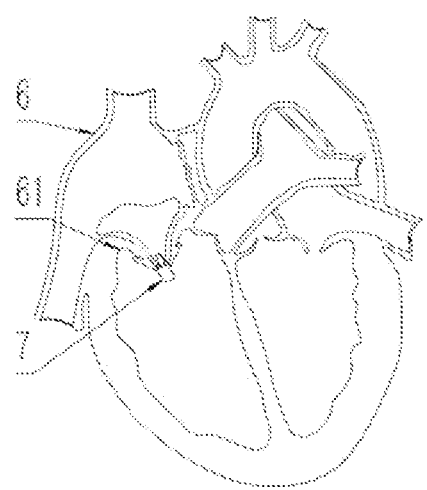
FIG. 12 is a schematic view of the repair device for treatment of tricuspid regurgitation after implantation according to the present disclosure.

The repair device for treatment of tricuspid regurgitation 7 can be implanted at the center of the leaflets 61 of the tricuspid valve in the right ventricle through the delivery system in a transthoracic or transfemoral manner (FIG. 12, delivery system not shown). In this embodiment, the occlusive membrane 2 may use a material and structure with desired biocompatibility and be able to promote endothelialization to accelerate the endothelialization of the leaflet and the repair device after operation and improve the safety of the device.

The above described are preferred embodiments of the present disclosure rather than limitations on the present disclosure in terms of form and substance. It should be noted that those of ordinary skill in the art may make various improvements and supplementations without departing from the principles of the present disclosure. However, these improvements and supplementations should be regarded as falling within the protection scope of the present disclosure. Those skilled in the art may make equivalent changes, such as alterations, modifications, and variations to the disclosed technical content without departing from the spirit and scope of the present disclosure, but they all constitute equivalent embodiments of the present disclosure. Any equivalent changes made to the embodiments according to the essential technology of the present disclosure, such as alterations, modifications, and variations, still fall within the scope of the technical solutions of the present disclosure.

What is claimed is:

1. A repair device for treatment of tricuspid regurgitation, delivered to leaflets of a tricuspid valve through a delivery system, comprising a support frame, an occlusive membrane, and a suture line, wherein the support frame comprises a central shaft and anchoring members that are disposed around the central shaft and radially unfolded for anchoring the leaflets of the tricuspid valve; the occlusive membrane surrounds connections between the anchoring members and the central shaft that are on an outer side wall of the central shaft, and the occlusive membrane is connected to the support frame through the suture line; a semi-closed space surrounding the central shaft is formed by the outer side wall of the central shaft, the anchoring members and the occlusive membrane, and the semi-closed space has a closed end in proximity to a ventricle and an open end in proximity to an atrium; and the central shaft has a closed end in proximity to the ventricle.

2. The repair device for treatment of tricuspid regurgitation according to claim 1, wherein the anchoring members each have one end fixedly connected to the central shaft and the other end radially unfolded away from the central shaft; the end of the anchoring member fixedly connected to the central shaft is provided with a hole for threading the suture line.

3. The repair device for treatment of tricuspid regurgitation according to claim 2, wherein the anchoring members comprise a plurality of clamp arm sets; the clamp arm set comprises two clamp arms, namely an upper clamp arm and a lower clamp arm, which are configured to cooperate with each other to open and close; the clamp arm is provided with barbs; the occlusive membrane is provided between any adjacent clamp arm sets around the central shaft; an edge of the clamp arm is provided with a hole for threading the suture line; and the clamp arm is further provided with a pull hole for threading a pull string configured to fold and unfold the clamp arm.

4. The repair device for treatment of tricuspid regurgitation according to claim 3, wherein the clamp arm comprises a fixed connection section with an end in proximity to the ventricle and fixedly connected to the central shaft and a separation section formed by extending from the fixed connection section to the atrium; and an edge of each of the fixed connection section, the separation section, and a transition section between the fixed connection section and the separation section is provided with a hole for threading the suture line.

5. The repair device for treatment of tricuspid regurgitation according to claim 4, wherein the hole for threading the suture line comprises a plurality of round holes or a slot hole.

6. The repair device for treatment of tricuspid regurgitation according to claim 5, wherein the support frame is integrally formed by cutting a metal tube, or by heat-setting a memory metal after laser cutting or wire cutting, and has a function of shape memory.

7. The repair device for treatment of tricuspid regurgitation according to claim 6, wherein the occlusive membrane is made of a flexible occlusive material and comprises an animal pericardial membrane, an animal valve membrane, a polyethylene terephthalate (PET) membrane, a polytetrafluoroethylene (PTFE) membrane, a polyurethane (PU) membrane, or a polyester fiber braided membrane.

8. The repair device for treatment of tricuspid regurgitation according to claim 7, wherein the suture line is made of nylon or a nitinol wire.

9. The repair device for treatment of tricuspid regurgitation according to claim 8, wherein the occlusive membrane is an integrally formed membrane and comprises a closed bottom cover for covering the end of the central shaft in proximity to the ventricle, a waist wrapping the outer side wall of the end of the central shaft in proximity to the ventricle, and branches between adjacent clamp arm sets; and alternatively, a transition portion is further provided between the waist and the branches.

10. The repair device for treatment of tricuspid regurgitation according to claim 8, wherein the occlusive membrane comprises a plurality of membrane sheets, and the plurality of membrane sheets are sutured to the support frame through the suture line.

* * * * *